Jan. 8, 1974 A. W. FISCHER Plant Pat. 3,428
AFRICAN VIOLET PLANT
Filed Jan. 24, 1972
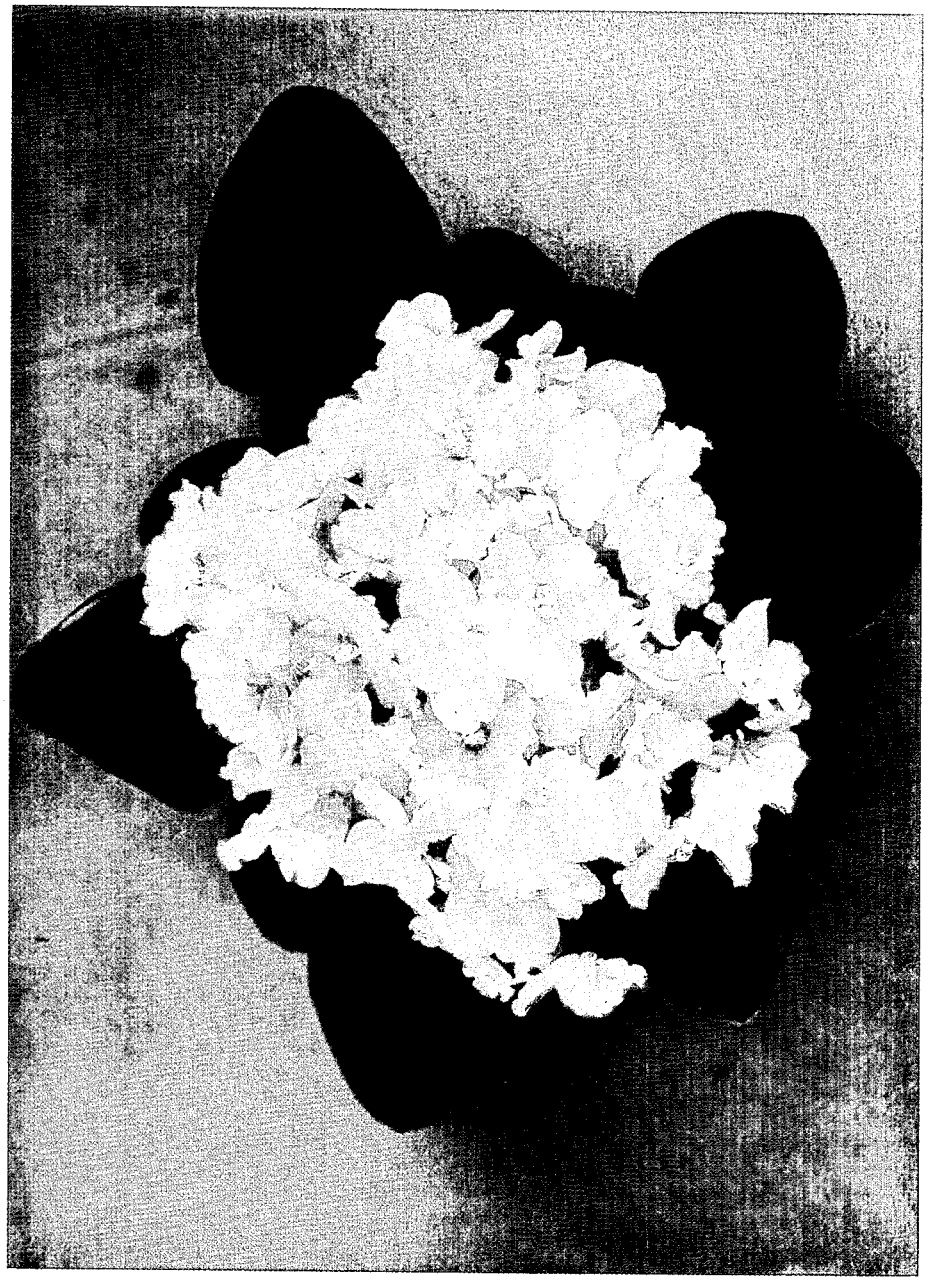

United States Patent Office

Plant Pat. 3,428
Patented Jan. 8, 1974

3,428
AFRICAN VIOLET PLANT

Arnold W. Fischer, Isernhagen, Germany, assignor to Geo. J. Ball, West Chicago, Ill.

Filed Jan. 24, 1972, Ser. No. 220,507
Int. Cl. A01h 5/00
U.S. Cl. Plt.—69 1 Claim

ABSTRACT OF THE DISCLOSURE

A new variety of African violet plant characterized by the delicate pink color of its very large blossoms which bloom profusely and recurrently the year around, and by its vigorous growth with abundant outwardly spreading foliage and relatively high display of closely massed flowers.

BACKGROUND OF THE INVENTION

My new variety of pink African violet plant was originated as a seedling in my greenhouses at Isernhagen, Germany, by crossing an unnamed double pink as the seed parent and an unnamed single pink as the pollen parent with the object of developing a more hardly and vigorously growing plant having a year around and profuse production of flowers, and a sturdier and more upright flower stalk displaying the flowers well above the foliage. This new variety of African violet plant satisfactorily fulfills these objectives and asexual propagation of this variety by me at Isernhagen, Germany, by means of leaf cuttings has shown the aforesaid characteristics to hold true from generation to generation and to be firmly fixed.

Commercial propagation of this new variety of African violet plant is now being done at West Chicago, Ill., U.S.A., by means of leaf cuttings and division of shoots with no noticeable deviation from the distinctive features of the original plant.

DESCRIPTION OF THE DRAWING

My new variety of African violet plant is illustrated by the accompanying drawing which shows the form and color characteristics of the plant, the color rendition being as nearly true as is reasonably possible to obtain by conventional photographic procedures.

DESCRIPTION OF THE NEW PLANT

The following is a detailed description of my new variety of African violet plant with color identification according to the Horticultural Colour Chart published by the British Colour Council in collaboration with the Royal Horticultural Society of London, England.

*The plant*

Origin: Seedling
Parentage:
- *Seed parent.*—A double pink (unnamed and unpatented)
- *Pollen parent.*—A single pink (unnamed and unpatented)

Classification:
- *Bontanic.*—*Saintpaulia* ionantha
- *Commercial.*—African violet Form: Compact potted plant (rosette arrangement)
Height. 3½ to 4 inches from base to top of flowers
Growth: Sturdy, vigorous and with very open foliage which tends to spread horizontally
Foliage: Quantity—abundant, but less compact than other varieties
- *Size of leaf.*—Up to 3 inches long and 2¾ inches wide
- *Shape of leaf.*—Oblong-ovate with crenate margins, some leaves having margins almost smooth

- *Texture.*—Smooth on upper side, coarse on under side and very tomentose on both sides
- *Veins.*—Pinnate. Very pronounced on under side and connecting at leaf margin.

Foliage:
- *Color.*—Upper side—Ivy Green 0001060/3. Under side—Dahlia Purple 931/1 with Veronese Green 660 showing through
- *Petioles.*—1¼ to 2 inches long in older leaves

*The bud*

Form: Urn-shaped, developing a mild point
Size: ¼ inch wide and ¼ inch long
Opening: Opens slowly, about five weeks from visible bud to opened flower
Color: When petals begin to unfurl—Orient Pink 416
Sepals: 5—Hooded over bud for a very short time
- *Form.*—Branched, upstanding and spear-shaped
- *Color.*—Inside—Sage Green 000861. Outside—Parsley Green 00962/1 with red tint Calyx:
- *Shape.*—Star-shaped when calyx splits
- *Aspect.*—Tomentose Peduncle:
- *Aspect.*—Very tomentose
- *Length.*—To 1¾ inches
- *Strength.*—Very flexible
- *Color.*—Purple Madder 1028 to Lavender Green 000761

*The flower*

Blooming character: Early, recurrent and profuse the year around
Size of flower: Very large. ⅞ to 1½ inches in diameter and up to ½ inch in depth
Borne: In cluster on primary peduncle or flower stalk
Shape: Very open cup changing to more flat with two small petals standing higher than other three
Petalage: 5 petals with 3 noticeably larger than others
- *Arrangement.*—Sympetalous
- *Form.*—Rotate and bilaterally symmetrical
- *Color.*—Upper side—Persian Rose 628/3. Under side—Rhodamine Pink 527/3
- *Texture.*—Soft
- *Appearance.*—Smooth and velvety. Tomentose on under side.
- *Petaloids.*—Occasionally one stamen has become petaloid. Size—3/16 to 7/16 inch long. Color—Rhodamine Pink 527/3 or 527/2

Peduncle: 1 3/16 to 1¾ inches to branching. 9/16 to ¾ inch to flower.
- *Strength.*—Very flexible
- *Color.*—Varies from Purple Madder 1028 to Lavender Green 000761

Discoloration after full bloom: Color fades greatly
Effect of climate: Hot climate supresses flowering. The plant thrives in 80 to 90% relative humidity.
Fragrance: Very slight
Lasting quality: 10 to 14 days after opening of flower
Persistence: Blossoms hang on and dry

*Reproductive organs*

Stamens:
- *Anthers.*—*Arrangement*—basifixed, 2 in number, each 1/16 inch long and having 2 anther cells
- *Filaments.*—Length—⅛ inch. Color—Citron Green 763/1 surrounded by Rhodamine Pink 527/2
- *Staminodes.*—Frequent and minute sterile stamens, occasionally some become petaloids
- *Pollen.*—Color—White Pistils: One, ⅜ inch long
Stigmas: Color—Erythrite Red 0027/1

Style:

*Length.*—3/16 inch

*Color.*—Rhodamine Pink 527/2

Ovaries: Superior and tomentose. Color—Pea Green 61

The principal distinctions of this new variety of African violet plant reside in the very large size of its light pink blossoms and the overall size of the plant whereby the mass of blossoms is displayed high above an open spread of relatively large, dark green, radially extending leaves. The plant blooms profusely the year around and begins its blooming somewhat earlier than other varieties of similar color which also enhances its commercial acceptance.

I claim:

1. A new variety of African violet plant, substantially as herein shown and described, characterized by the very large size of its light pink blossoms, the relatively large size of the plant, the height at which the blossoms are displayed and the early and profuse production of its flowers.

No references cited.

ROBERT E. BAGWILL, Primary Examiner